(12) United States Patent
Deslys et al.

(10) Patent No.: US 6,806,077 B1
(45) Date of Patent: Oct. 19, 2004

(54) METHOD FOR SCREENING SUBSTANCES WITH THERAPEUTIC ACTION IN THE TREATMENT OF TRANSMISSABLE SUBACUTE SPONGIFORM ENCEPHALOPATHIES

(75) Inventors: Jean-Philippe Deslys, La Celle Saint Cloud (FR); Vincent Beringue, Thiverval Grignon (FR); Corinne Lasmezas, Paris (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/341,539

(22) PCT Filed: Jan. 14, 1998

(86) PCT No.: PCT/FR98/00063

§ 371 (c)(1),
(2), (4) Date: Oct. 12, 1999

(87) PCT Pub. No.: WO98/30909

PCT Pub. Date: Jul. 16, 1998

(30) Foreign Application Priority Data

Jan. 14, 1997  (FR) ............................................. 97 00278

(51) Int. Cl.[7] ................................................ C12N 7/02
(52) U.S. Cl. ................... 435/239; 435/235.1; 435/68.1; 435/5; 530/350
(58) Field of Search ............................. 435/239, 235.1, 435/68.1, 5; 530/350

(56) References Cited

U.S. PATENT DOCUMENTS 5,276,059 A  1/1994 Caughey et al. ............ 514/647

5,834,593 A  * 11/1998 Prusiner et al. ............. 530/350

FOREIGN PATENT DOCUMENTS

WO    WO 93/23432    11/1993

OTHER PUBLICATIONS

Debbie McKenzie et al., Amphotericin B Delays both Scrapie Agent Replication and PrP–res Accumulation Early in Infection, Journal of Virology, Nov. 1994, pps. 7534–7536, vol. 68, No. 11.
Suehiro Sakaguchi et al., Accumulation of Proteinase K–Resistant Prion Protein (PrP) Is Restricted by the Expression Level of Normal PrP in Mice Inoculated with a Mouse–Adapted Strain of the Creutzfeldt–Jakob Disease Agent; Journal of Virology, Dec. 1995, pps. 7586–7592, vol. 69, No. 12.
Robert B. Petersen et al., Effect of the D178N Mutation and the Codon 129 Polymorphism on the Metabolism of the Prion Protein, Journal of Biological Chemistry, vol. 271, No. 21, May 24, 1996, pp. 12661–12668, 1996.
McKenzie, D., et al., 1994, "Amphotericin B delays both scrapie agent replication and PrP–res accumulation early in infection", J. Virol. 68(11):7534–7536.*

* cited by examiner

Primary Examiner—Jeffrey S. Parkin
(74) Attorney, Agent, or Firm—Morgan Lewis & Bockius LLP

(57) ABSTRACT

The invention concerns a method for screening substances capable of having therapeutic action in the treatment of transmissible subacute spongiform encephalopathy (TSSE) or prion diseases comprising a step of isolating the PrPres, from the spleen, methods for isolating the PrPres, particularly adapted to said screening method and their applications, in particular for detecting PrPres.

14 Claims, 6 Drawing Sheets

METHOD FOR SCREENING SUBSTANCES WITH THERAPEUTIC ACTION IN THE TREATMENT OF TRANSMISSABLE SUBACUTE SPONGIFORM ENCEPHALOPATHIES

The present invention relates to a method for screening substances capable of having a therapeutic action in the treatment of transmissible subacute spongiform encephalopathies (TSSEs) or so-called prion diseases, which comprises a step of isolating the PrPres from the spleen; the present invention also relates to methods for isolating the PrPres, which are particularly suited to the said screening method, and their applications in particular in the detection of PrPres.

Transmissible subacute spongiform encephalopathies are caused by nonconventional transmissible agents (NCTAs), also called prions, whose precise nature remains unknown to date. TSSEs comprise essentially Creutzfeldt-Jakob disease, in humans (CJD), scrapie, in sheep and goats, and bovine spongiform encephalopathy (BSE), in bovines; other encephalopathies have been demonstrated in mink or some wild animals such as red deer and elk.

The progression of these diseases is always fatal and there is currently no effective treatment.

In transmissible subacute spongiform encephalopathies, there is an accumulation of a host protein, PrP (or prion protein), in an abnormal form (PrPres), mainly in the central nervous system; PrPres copurifies with the infectivity and its accumulation precedes the appearance of histological lesions. In vitro, it is toxic for neuron cultures.

Two biochemical properties make it possible to distinguish PrPres from the normal PrP: PrPres is partially resistant to proteases and is insoluble in nonionic detergents such as Triton-X100.

The search for new molecules which may be effective in the treatment of these encephalopathies is hindered both by the absence of efficient in vitro models and the length of time for setting up in vivo experimental models, such as experimental scrapie in hamsters (80 to 365 days), or experimental scrapie in mice (180 to 550 days).

Consequently, the inventors set themselves the objective of providing an effective and reliable method of screening which does not exhibit the disadvantages of the experimental models currently used and which is more suitable for the requirements of practical use, in particular in that the evaluation of the action of the substances to be tested can be carried out in less than two months.

To do this, the inventors have found a reliable marker and have developed a reproducible protocol.

The subject of the present invention is a method for screening substances capable of having therapeutic action in the treatment of transmissible subacute spongiform encephalopathies (TSSEs or so-called prion diseases), characterized in that it comprises the following steps:

a) inoculation at time $t_A$, into at least one laboratory animal such as a rodent, mouse or hamster (preferably several, divided into batches), by any appropriate route, of a nonconventional transmissible agent (NCTA) or prion;

b) administration to the said laboratory animal, by any appropriate route, of either a substance to be screened (test animal), or of a placebo (negative control animal), within a period between $t_A$−15 days and $t_C$, corresponding to the time when the PrPres level in the spleen of the said laboratory animal is at maximum or within a period between $t_B$, corresponding to the time of the first detection of PrPres in the spleen of the said laboratory animal and $t_C$; $t_B$ being between $t_A$ and $t_A$+15 and $t_C$ being between $t_A$+20 and $t_A$+30, preferably between $t_A$+25 and $t_A$+30;

c) sacrificing of the animals within a time interval between $t_B$ and $t_C$, preferably at $t_C$, and collecting of the spleen;

d) isolation of the PrPres from the spleens collected, according to a suitable method of isolation comprising the homogenization of the spleen, followed by a specific extraction of the PrPres comprising a single separation step, from the homogenate obtained, and optionally the purification of the PrPres;

e) semiquantification of the PrPres obtained in step (d) by detection of the said PrPres by any appropriate method, producing a specific signal, followed by a comparison of the signal obtained with a calibration series of dilutions of a positive control consisting of a brain homogenate from an animal at the terminal stage of the disease; and f) selection of the screened substances as a candidate for the treatment of transmissible subacute spongiform encephalopathies, if the PrPres, level obtained in the spleen of the test animal, in step e), is reduced by at least a factor of 2 compared with the level obtained under the same conditions with the negative control animal.

The times $t_A$, $t_B$ and $t_C$ are expressed in days; $t_A$=D0.

Indeed, the inventors have found, unexpectedly, that substances which increase the survival of infected animals, regardless of the mode of inoculation (peripheral or intracerebral), also result in a delay in the accumulation of PrPres in the spleen, detected under standardized conditions.

Standardized conditions are understood to mean, for the purposes of the present invention, conditions in which the following parameters are selected:

NCTA selected, route of administration of NCTA, method of isolation of the PrPres from the spleen.

For a strain selected from a given animal, at the terminal stage of the disease, the infectious titer is constant.

The detection of PrPres in the spleen makes it possible to observe much more rapidly the effects of the molecules to be tested, in particular the inhibition of the accumulation of PrPres, either within the hours following the inoculation (capture of the inoculum by the spleen and detection of a PrPres peak between $t_A$ and $t_A$+1–2 days), or between 5 and 15 days after the infection; $t_B$ corresponds both to the detection of the peak at the time of capture of the inoculum and to the detection of the neosynthesized PrPres; this is the reason why $t_B$ is between $t_A$ and $t_A$+15; these $t_B$ and $t_C$ values may vary within the ranges defined above, depending on the NCTA and the laboratory animal (mouse) selected; for example, when the UCTA corresponds to the murine strain C506M3 inoculated by the intraperitoneal route, in the C57BL/6 mouse, the neosynthesized PrPres may be detected in 100% of cases, from the 5th day post-infection (p.i.) ($t_B$) and a plateau is observed from the 30th day p.i. ($t_C$).

Such a method therefore makes it possible to select molecules capable of preventing the accumulation of PrPres; such molecules are considered to be capable of exhibiting therapeutic action in the treatment of TSSEs.

In accordance with the invention:

In step a):

the NCTA corresponds to a strain stabilized in the host animal, that is to say which exhibits stable characteristics in this host animal after several passages and in particular the following characteristics: identical period before the appearance of the disease and identical lesional profile during passages in all animals (degree of vacuolation of various parts of the brain); it corresponds to any strain stabilized under the abovementioned conditions, inducing a premature accumulation of PrPres in the spleen of the host animal, such as scrapie strains or bovine encephalopathy strains, in particular the scrapie strains called Chandler, ME7, 139A (M. E. Bruce et al., Scrapie strain variation and its implication in *Current topics in Microbiology and Immunology: Transmissible Spongiform Encephalopathies, Scrapie, BSE and related disorders,* 1991, 172, 125–138), C506M3 (C. I.

Lasmézas et al., J. Gen. Virol., 1996, 77, 1601–1609) or 263K (R. H. Kimberlin et al., J. Gen. Virol., 1977, 34, 295–304 and 1978, 39, 487–496) or the BSE strains called 4PB1 (C. I. Lasmézas et al., 1996, cited above) and 301V (C. F. Farquhar et al., J. Gen. Virol., 1996, 77, 1941–1946);

the said NCTA is preferably administered in a buffer suited to the route of administration selected in the form either of a crude tissue, preferably brain, homogenate, or of a PrPres pellet, obtained by appropriate centrifugation, from a crude tissue, preferably brain, homogenate;

the said NCTA may be administered by any route (oral route, parenteral route), preferably by the intraperitoneal route, at a dose corresponding to an inoculum of NCTA, between 0.001% and 10% (weight/volume) ($LD_{50}$ between $10^3$ and $10^7$);

the said laboratory animal is preferably a rodent (mouse or hamster, for example).

In step b):

the substance to be screened is administered by the oral or parenteral route;

if the treatment is started between $t_B$ and $t_C$, (that is to say when the PrPres in the spleen is constantly detectable), the model according to the invention makes it possible to study only the action of the substance to be screened on the NCTA inoculated during replication at the sites of replication (target cells), whereas if it is administered before $t_B$, for example at $t_A$, the model according to the invention makes it possible to study, in addition, the action of the substance to be screened before the NCTA has reached its target cells in the spleen.

In step d):

depending on the sequence of steps selected among the known protein isolation techniques, namely the methods based on molecular size, such as centrifugation, the methods based on differences in solubility such as salting in and salting out or fractionation by solvents or the methods based on electrical charge, the degree of purification and the yield will be different. Within the framework of the present invention, it is necessary to select a reliable and sensitive method which makes it possible to obtain a detection threshold such that the ratio: maximum level detectable in the spleen/cut off is as high as possible, preferably greater than 2 or such that when a ½ dilution of the final sample obtained is carried out, a detection signal is still obtained;

sequences of steps preferred are described hereinafter: they have the advantage, over the methods of isolation previously described, of having high reliability and high sensitivity, because the actual extraction comprises only a single separation step and because of the particular selection of the sequence of steps, whereas in the methods previously described (R. E. Race et al., J. Gen. Virol., 1992, 73, 3319–3323; Doi et al., J. Gen. Virol., 1988, 69, 955–960; T. Muramoto et al,. Am. J. Pathol., 1993, 143, 5 1470–1479; Farquhar C. F. et al., Gen. Virol., 1994, 75, 495–504 and J. Gen. Virol., 1996, 77, 1941–1946), the extraction comprises several separation steps and leads to an imprecision as regards the quantification, and/or the sensitivity of these methods is insufficient to obtain a fine detection threshold and a fine quantification and in particular to effectively detect a large variation in the PrPres level.

In step e):

the PrPres is in particular detected by immunoassay (Western blot for example).

The subject of the present invention is also a method for isolating PrPres, from an organ or a tissue, in particular the spleen or the brain, characterized in that it comprises essentially the following steps:

(i) homogenization of organ or tissue, collected after sacrificing the animal, by mechanical grinding in a homogenization buffer, followed by calibration of the homogenate, for the production of a homogenate comprising, in weight/volume, from 5 to 50% of the said organ or tissue;

(ii) specific extraction of PrPres comprising a single separation step, by treating the homogenate obtained in step (i) by incubating the suspension obtained with a protease and an anionic detergent (surfactant), capable of promoting the aggregation of the PrPres, such as 10–30% sarkosyl (lauroyl sarcosine) in a suitable buffer and separation of the PrPres, by a single ultracentrifugation at 480,000–1,200,000 g.h, preferably for 2–4 hours, for example at 240,000–300,000 g for 2 to 4 h, preferably at 20–22° C., of the suspension obtained, deposited on a buffer cushion having a density of between 1.02 and 1.08, at 20° C. and recovering the centrifugation pellet comprising the said PrPres; and, if necessary, (iii) purification of the PrPres by suspending the centrifugation pellet obtained in (ii) in a Laemmli buffer comprising 1–5% SDS, incubating in this buffer at 100° C. for 2–10 minutes and centrifuging at 12,000–15,000 g for 10–15 minutes at 16–22° C.

The said PrPres thus purified may then be separated by any appropriate technique such as electrophoresis (polyacrylamide gel electrophoresis, for example) or immunocapture, from the centrifugation supernatant.

In accordance with this method, the homogenization buffer in step (i) is in particular a neutral buffer such as water or an isotonic buffer such as 5% glucose.

Also in accordance with the invention, during the extraction step (ii), the ultracentrifugation is carried out after depositing the suspension containing the PrPres on a 6–20% sucrose cushion.

As a variant, the subject of the present invention is also a method in which the extraction comprises a single step for the preparation of the PrPres, and does not require ultracentrifugation; such a method for isolating PrPres, from an organ or tissue, in particular the spleen or the brain, is characterized in that it comprises essentially the following steps:

(i) homogenization of organ or tissue, collected after sacrificing the animal, by mechanical grinding in a homogenization buffer, followed by the addition, to the homogenate obtained, of a salt having a high ionic strength and capable of promoting the aggregation of the PrPres, such as 10–30% NaCl, in a 1:1 (v/v) ratio, followed by calibration of the homogenate, for the production of a homogenate comprising, in weight/volume, from 5 to 50% of the said organ or tissue;

(ii) specific extraction of PrPres by treating the homogenate obtained in step (i) by incubating the suspension obtained with a protease and an anionic detergent capable of promoting the aggregation of the PrPres, such as 10–30% sarkosyl and a single separation of the PrPres, by centrifugation at 25,000–60,000 g.h, for example at 25,000–30,000 g for 1 to 2 h, preferably at 16–22° C., of the suspension obtained, deposited on a buffer cushion having a density of between 1.02 and 1.08, at 20° C., and recovering the centrifugation pellet comprising the said PrPres; and, if necessary, (iii) purification of the PrPres by suspending the centrifugation pellet obtained in (ii) in a Laemmli buffer comprising 1–5% SDS, incubating in this buffer at 100° C. for 2–10 minutes and centrifuging at 12,000–15,000 g for 10–15 minutes at 16–22° C.

The said PrPres thus purified may then be separated by any appropriate technique such as electrophoresis (polyacrylamide gel electrophoresis, for example) or immunocapture, from the centrifugation supernatant.

In accordance with this method, the homogenization buffer in step (i) is in particular a neutral buffer such as water or an isotonic buffer such as 5% glucose.

Also in accordance with the invention:

during the extraction step (ii), the solution used for the extraction comprises an anionic detergent capable of promoting the aggregation of the PrPres and a detergent having protein-renaturing properties, such as a zwitterionic detergent, such as a sulphobetaine, preferably the sulphobetaine SB 3–14 at 1–2%, in a 1:1 (v/v) ratio;

during the extraction step (ii), but prior to the centrifugation, at least one protease inhibitor is added;

the centrifugation depending on the extraction step (ii) is preferably carried out after depositing the suspension containing the PrPres on a 6–20% sucrose cushion or a 6–20% sucrose cushion and a sulphobetaine.

The PrPres can then be detected by any appropriate specific method.

Surprisingly, these methods for isolating PrPres, from the spleen, comprising an extraction in a single step, do not bring about a cumulative loss of PrPres and can be directly used without modification, to extract the PrPres from any other tissue.

In addition to the preceding features, the invention also comprises other features, which will emerge from the description which follows, which refers to exemplary embodiments of the method which is the subject of the present invention and to the accompanying drawings in which.

Figure 3:
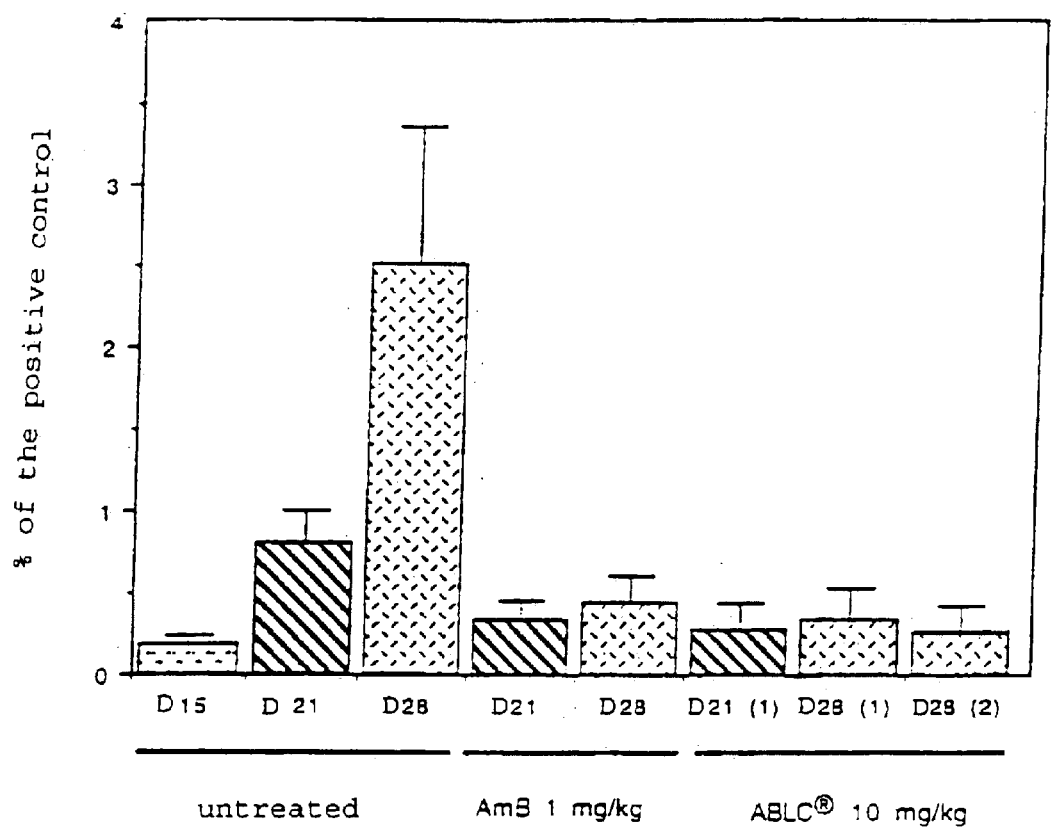
Figure 4:
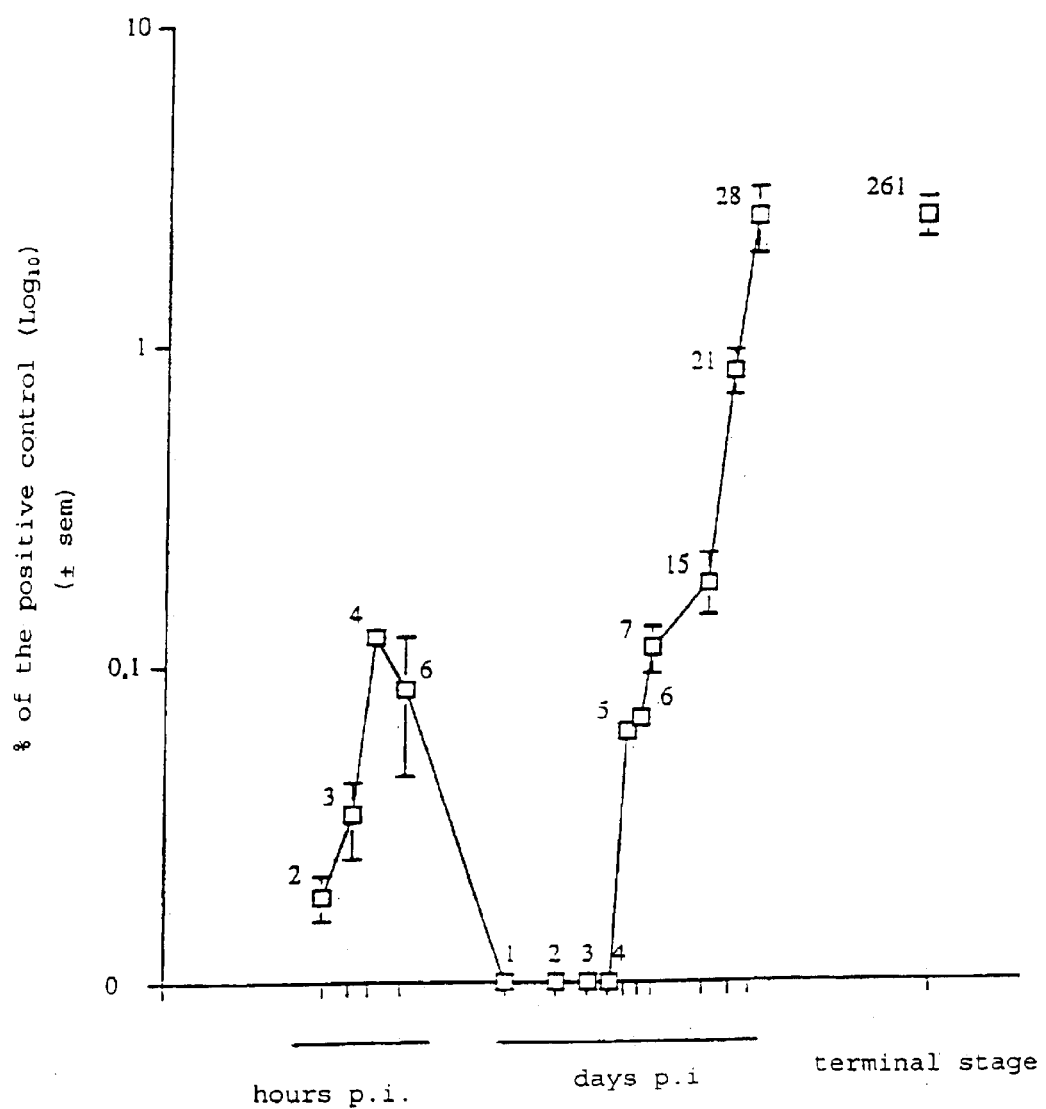
Figure 5:
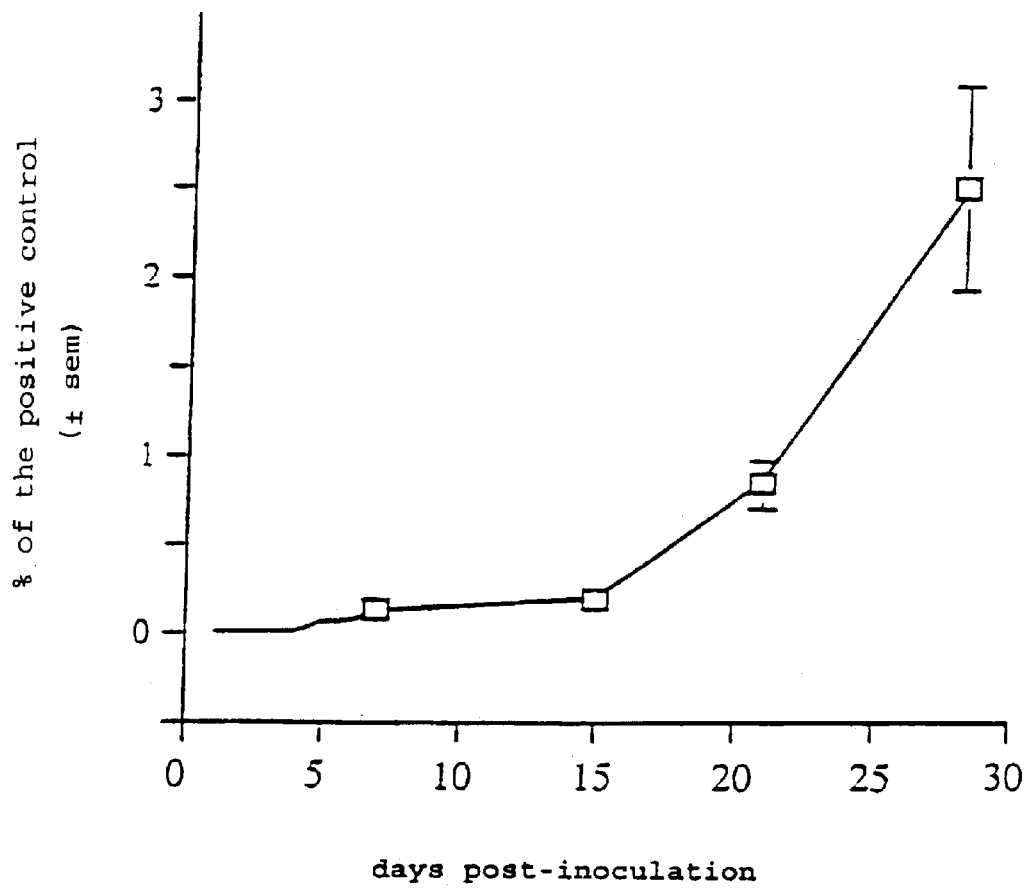
Figure 6:
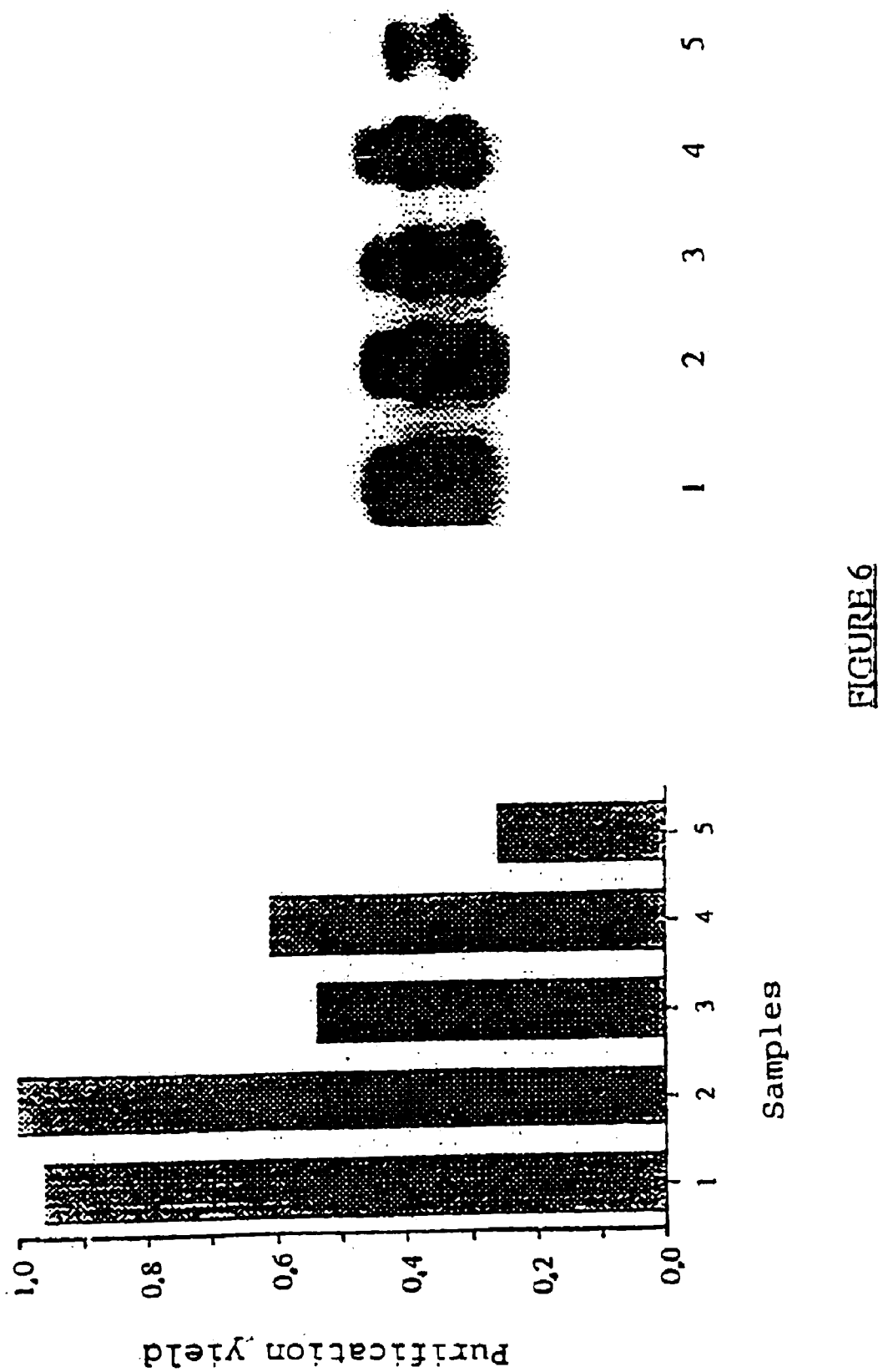
Figure 7:
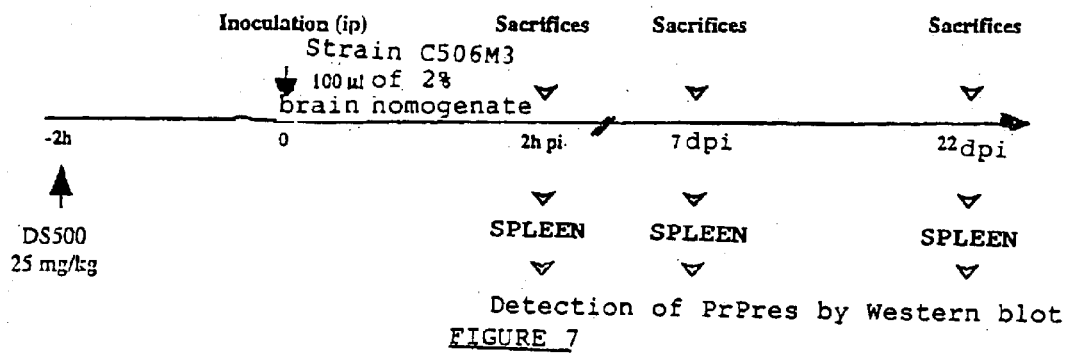
Figure 8:
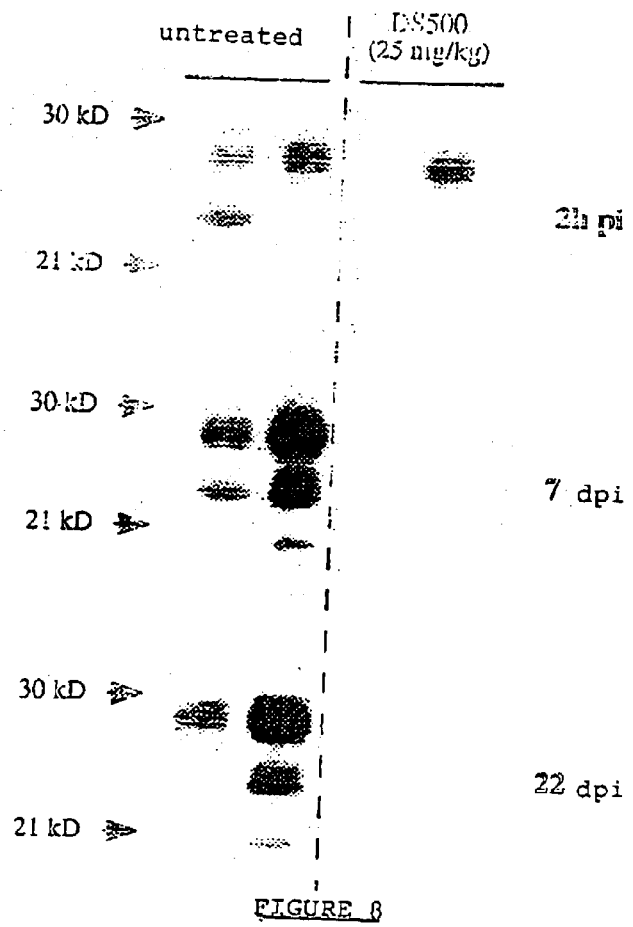

FIG. 3, in the form of a histogram, illustrates the inhibition of the accumulation of PrPres in the same mouse, after treatment with amphotericin B or ABLC® (AmB Lipid Complex), compared with a negative control animal, treated with a placebo and in which there is no inhibition of the said accumulation;

FIGS. 4 and 5 illustrate the kinetics of accumulation of PrPres in the spleen of C57BL/6 mice inoculated i.p. with the strain C506M3 (0–28 days post-inoculation);

FIG. 6 illustrates the role of the composition of the extraction buffer in the purification yield of PrPres;

FIG. 7 illustrates the treatment protocol carried out to test dextran sulphate (DS500);

FIG. 8 illustrates the accumulation of PrPres in spleens of C57BL/6 mice infected by the intraperitoneal route with the C506M3 strain and treated 2 h before inoculation with dextran sulphate DS500.

It should be understood, however, that these examples are given solely by way of illustration of the subject of the invention and do not constitute in any manner a limitation thereto.

EXAMPLE 1

Study of the accumulation of PrPres in spleens of C57BL/6 mice infected by the intraperitoneal (ip) route with the C506M3 strain and treated for 1 or 2 weeks (6 days/week), from $t_A+15$ after inoculation, with amphotericin B (AmB) and its derivatives; isolation of the PrPres present in the spleen by the method of isolation comprising an ultracentrifugation, as described above.

Step a) of the method of screening: inoculation at $t_A$, C57BL/6 mice are inoculated by the intraperitoneal route with 100 µl of 2% brain homogenate in 5% glucose, from an infected mouse at the terminal stage of experimental scrapie (strain C506M3).

Figure 1:
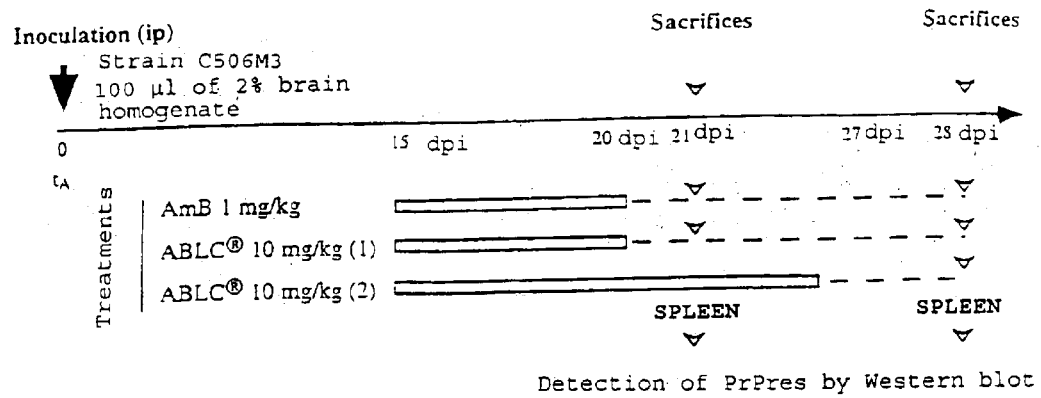
FIG. 1 illustrates the protocol used in a method of screening according to the invention.

Step b) of the method of screening: administration of a substance capable of having a therapeutic action or administration of a placebo at $t_A+15$ days (→ period between $t_B$ and $t_C$), the C57BL/6 mice are, divided into various batches and are treated:

either with amphotericin B, at the rate or 1 mg/kg (AmB), or with ABLC®, at the rate of 10 mg/kg, for 6 days (1) or 12 days (2), in accordance with FIG. 1, or with a placebo.

Step c) of the method of screening: sacrificing the animals.

At $t_A+21$ days (→ period between $t_B$ and $t_C$) or at $t_A+28$ days (→ at $t_C$) the mice are sacrificed by breaking the cervical vertebrae; the spleens are immediately collected, in accordance with FIG. 1, and either stored at −80° C., or used while fresh.

Step d) of the method of screening: isolation of the PrPres

The spleens collected are ground and homogenized at 10% (weight/volume) in a 5% glucose solution. The homogenate obtained is calibrated by passing through a suitable syringe.

The 10% homogenate (200 µl) is then treated with proteinase K (10 µg/ml), at 37° C., for one hour; the digestion is blocked with the aid of 5 mM phenylmethylsulphonyl fluoride (PMSF). After addition of 20% sarkosyl in 10 mM Tris, pH 7.4, the samples are incubated for 15 minutes at room temperature They are then centrifuged at 245,000 g for 4 hours at 20° C., on a 10% sucrose cushion (100–300 µl) (Beckman TL100 ultracentrifuge).

The pellets are resuspended in a Laemmli buffer, incubated for 5 minutes at 100° C., and then the samples obtained are subjected to centrifugation at 15,000 g, for 15 minutes at 16° C.

Figure 2:
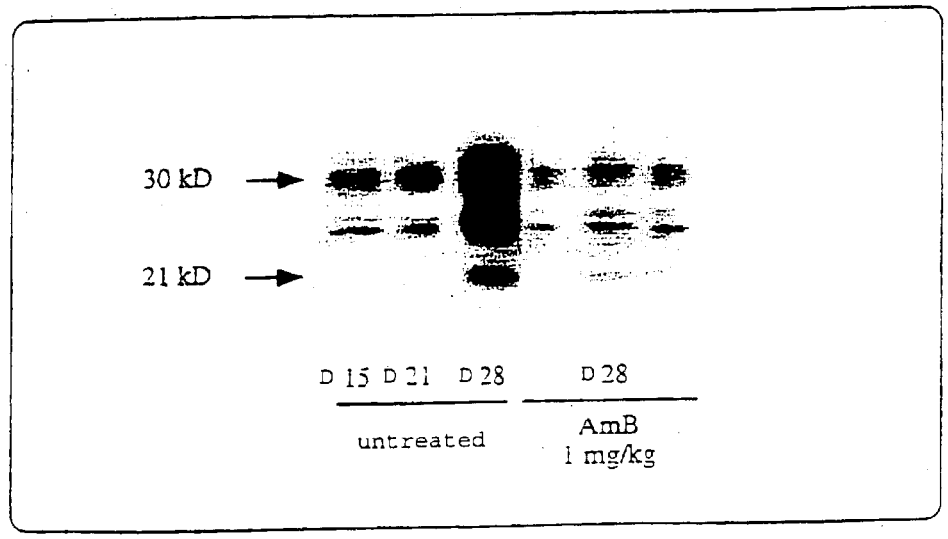
FIG. 2 represents a polyacrylamide gel showing the inhibition of the accumulation of PrPres in the spleens of mice infected with the strain C506M3 and treated with amphotericin B (AmB) (the molecular weight ladder was established with Amersham prestained markers)

Step e) of the method of screening according to the invention: detection of the PrPres in the samples The samples obtained are used to carry out an SDS-PAGE electrophoresis (12% polyacrylamide gel loaded with the equivalent of 10 mg of spleen) and transferred to a nitrocellulose membrane, under the conditions described by Towbin et al. (Proc. Natl. Acad. Sci. USA, 1979, 76, 4350–4354) or by C. I. Lasmézas et al. (J. Gen. Virol., 1996, cited above). The immuunodetection of the PrPres was carried out with the antiserum 007 JB (R. Demaimay et al., Journal of Virology, 1997, 71, 12, 9685–9689), directed against the peptide 90–108 of the murine PrP at 1/2500) and peroxidase-conjugated anti-rabbit goat Ig's (1/2500). The immunoreactivity is revealed by chemiluminescence (ECL, Amersham), quantified and visualized on autoradiography films, as illustrated in FIG. 2, for the untreated animals and the animals treated for 6 days with AmB at 1 mg/kg and sacrificed at $t_A+28$ days, that is to say one week after the end of the treatment.

The antibodies are obtained by coupling the said peptide (Néosystem, Strasbourg) to KLH, followed by subcutaneous injection into the dorsal region of "New Zealand" rabbits of an emulsion comprising the said coupled peptide and of complete Freund's adjuvant (R. Demaimay et al., Journal of Virology, 1997, 71, 12, 9685–9689).

Step f) of the method of screening according to the invention: selection of the screened substance FIG. 3 illustrates the results obtained for the untreated animals, the animals treated with AmB; 1 mg/kg sacrificed at $t_A+21$ or at $t_A+28$ and the animals treated with ABLC® 6 days (1) or 12 days (2) and sacrificed at $t_A+21$ or at $t_A+28$: both for the animals treated with AmB and with ABLC®, a significant inhibition of the accumulation of PrPres is observed; to construct the histogram, the quantities of PrPres detected in the spleen are compared with a linear series of dilutions of purified PrPres according to the same method as that described above, from a brain homogenate of animals at the terminal stage of the disease (positive control).

FIGS. 4 and 5 illustrate the kinetics of accumulation of PrPres in the spleen of C57BL/6 mice, inoculated with the C506M3 strain at $t_A$, under the same conditions as above, for 28 days, and untreated: a gradual increase is observed up to $t_A+30$ to (→ at $t_C$); a plateau is observed from $t_A+30$.

EXAMPLE 2

Study of the accumulation of PrPres in spleens of C57BL/6 mice infected by the intraperitoneal (ip) route with the C506M3 strain and treated for 1 or 2 weeks (6 days/week), from $t_A+15$ after inoculation, with amphotericin B (AmB) and its derivatives; isolation of the PrPres by the method including no ultracentrifugation.

Steps a), b), c), e) and f) are identical to those of Example 1.

Step d) of isolation of the PrPres from the spleens of mice is carried out as follows:

The spleens collected are ground and homogenized at 20% (weight/volume) in a solution containing 5% glucose; 200 µl of 20% NaCl are added to 200 μl of homogenate (1:1, v/v). The homogenate obtained is calibrated by passing through a suitable syringe.

200 μl of detergent (20% sarkosyl and 2% sulphobetaine (SB3.14 Calbiochem)) and proteinase K at 10 μg/ml are added to 200 μl of 20% homogenate, and then the mixture is incubated at 37° C., for one hour.

The samples are then centrifuged at 30,000 g for 2 hours at 22° C., on 200 μl of a cushion comprising 10% sucrose and 0.1% sulphobetaine, as final concentrations (Eppendorf rotor; ALC 4239R centrifuge).

FIG. 6 illustrates the purification yields obtained with various extraction buffer compositions (representation in the form of a histogram and of a Western blot): 1: yield control (total homogenate); 2: 10% sarkosyl/10% NaCl/10 mM Tris/1% SB3-14; 3: 10% sarkosyl/10% NaCl/10 mM Tris; 4: 10% sarkosyl/10% NaCl; 5: 10% sarkosyl.

The pellets are resuspended in a Laemmli buffer, incubated for 5 minutes at 100° C., and then the samples obtained are subjected to a second centrifugation at 15,000 g, for 15 minutes at 16° C.

EXAMPLE 3

Study of the accumulation of the PrPres in spleens of C57BL/6 mice infected by the intraperitoneal route with the C506M3 strain and treated at $t_A$2 hours with dextran sulphate (DS500).

The treatment protocol is summarized in FIG. 7.

Step b) of the method of screening: administration of a substance capable of having a therapeutic action.

At $t_A$2hours (that is to say 2 hours before the inoculation of the infectious strain), C57BL/6 mice are divided into various batches:

untreated mice and mice treated with dextran sulphate (DS500) at 25 mg/kg (single injection at $t_A$2 hours).

Step a) of the method of screening: inoculation

At $t_A$, the C57BL/6 mice are inoculated by the intraperitoneal route with 100 μl of 2% brain homogenate in 5% glucose, from an infected mouse at the terminal stage of experimental scrapie [strain C506M3].

Step c) of the method of screening: sacrificing the animals

At $t_A$+2 hours, $t_A$+7 days and $t_A$+22 days, the mice are sacrificed by breaking the cervical vertebrae; the spleens are immediately collected.

Step d) of the method of screening: isolation of the PrPres identical to step d) of Example 2.

Step e) of the method of screening according to the invention: detection of the PrPres in the samples.

The samples obtained are used to carry out an SDS-PAGE electrophoresis (12% polyacrylamide gel loaded with the equivalent of 40 mg of spleen for 2 h and 7 days and 10 mg of spleen for 22 days) and transferred to nitrocellulose membrane, under the conditions described by Towbin et al. (Proc. Natl. Acad. Sci. USA, 1979, 76, 4350–4354) or by C. I. Lasmézas et al. (J. Gen. Virol., 1996, cited above). The immunodetection of the PrPres was carried out with the antiserum 007JB (R. Demaimay et al., J. Virol. 1997, 71, 12, 9685–9689) at 1/5000th, and peroxidase conjugated anti-rabbit goat Ig's (1/2500). The immunoreactivity is revealed by chemiluminescence (ECL, Amersham), quantified and visualized on autoradiography films, as illustrated in FIG. 8, for the untreated animals and the animals treated 2 h before the inoculation with DSSOO and sacrificed at $t_A$+2 h, $t_A$+7 days and $t_A$+22 days.

Step f) of the method of screening according to the invention: selection of the screened substance FIG. 8 illustrates the results obtained; a significant inhibition of the accumulation of PrPres is observed in the treated animals.

As is evident from the above, the invention is not at all limited to those of its embodiments, implementations and applications which have just been described more explicitly; it embraces on the contrary all the variants thereof which may occur to the specialist in this field, without departing from the framework or the scope of the present invention.

What is claimed is:

1. A method of isolating PrPres, from an organ or a tissue, in particular the spleen or the brain, consisting essentially of:

(i) homogenization of organ or tissue, collected after sacrificing the animal, by mechanical grinding in a homogenization buffer, followed by the addition, to the homogenate obtained, of a salt having a high ionic strength and capable of promoting the aggregation of the PrPres in a 1:1 (v/v) ratio, followed by calibration of the homogenate, for the production of a homogenate comprising, in weight/volume, from 5 to 50% of the said organ or tissue; and (ii) specific extraction of PrPres by treating the homogenate obtained in step (i) by incubating the suspension obtained with a solution comprising a protease and an anionic detergent capable of promoting the aggregation of the PrPres, and a single separation of the PrPres, by centrifugation at 25,000–60,000 g.h, of the suspension obtained, deposited on a buffer cushion having a density of between 1.02 and 1.08, at 20° C. and recovering the centrifugation pellet comprising the said PrPres.

2. The method according to claim 1, wherein during the extraction step (ii) the solution used for the extraction comprises an anionic detergent capable of promoting the aggregation of the PrPres and a zwitterionic detergent, in a 1:1 (v/v) ratio.

3. The method according to claim 1, wherein in the extraction step (ii) the centrifugation is carried out after depositing the suspension containing the PrPres on a cushion comprising, in a mixture, 6–20% sucrose and a sulphobetaine.

4. The method according to claim 1, wherein the homogenization buffer in step (i) is a neutral buffer selected from the group consisting of water and isotonic buffers.

5. The method of claim 4, wherein the isotonic buffer is 5% glucose.

6. The method of claim 1, wherein in step (i), the salt having a high ionic strength is 10–30% NaCl.

7. The method of claim 1, wherein in step (ii), prior to centrifigation, at least one protease inhibitor is added.

8. The method of claim 1, wherein the anionic detergent is 10–30% sarkosyl.

9. The method of claim 1, wherein in step (ii), the centrifugation is carried out after depositing the suspension containing the PrPres on a 6–20% sucrose cushion.

10. The method of claim 1, wherein in step (ii) the centrifugation is carried out at 25,000–30,000 g for 1 to 2 hours.

11. The method of claim 1, wherein in step (ii) the centrifugation is carried out at 16–22° C.

12. The method of claim 1, further comprising the step consisting essentially of: purification of the PrPres by suspending the centrifugation pellet obtained in (ii) in a Laemmli buffer comprising 1–5% SDS, incubating in this buffer at 100° C. for 2–10 minutes and centrifuging at 12,000–15,000 g for 10–15 minutes at 16–22° C.

13. The method of claim 2, wherein the zwitterionic detergent is a sulphobetaine.

14. The method of claim 13, wherein the sulphobetaine is the sulphobetaine SB3-14 at 1–2%.

* * * * *